United States Patent
Min et al.

(10) Patent No.: US 12,114,880 B1
(45) Date of Patent: Oct. 15, 2024

(54) THROMBECTOMY DEVICE HAVING OPEN FRAME CELL RING

(71) Applicant: Nventric Corporation, Seoul (KR)

(72) Inventors: Sungwoo Min, Fullerton, CA (US); Don Quy Ngo, Los Angeles, CA (US)

(73) Assignee: NVENTRIC CORPORATION, Seoul (KR)

( * ) Notice: Subject to any disclaimer, the term of this patent is extended or adjusted under 35 U.S.C. 154(b) by 0 days.

(21) Appl. No.: 18/230,128

(22) Filed: Aug. 3, 2023

(51) Int. Cl.
*A61B 17/221* (2006.01)

(52) U.S. Cl.
CPC .... *A61B 17/221* (2013.01); *A61B 2017/2212* (2013.01); *A61B 2017/2215* (2013.01)

(58) Field of Classification Search
CPC ........ A61B 17/22031; A61B 17/22032; A61B 17/221; A61B 2017/22034; A61B 2017/22035; A61B 2017/2212; A61B 2017/2215; A61B 2017/2217; A61F 2/82; A61F 2/852; A61F 2/86; A61F 2/88; A61F 2/885; A61F 2/89; A61F 2/90; A61F 2/91; A61F 2/915; A61F 2/92; A61F 2/93
USPC ...................................................... 606/159
See application file for complete search history.

(56) References Cited

U.S. PATENT DOCUMENTS

| | | | |
|---|---|---|---|
| 8,777,976 B2 | 7/2014 | Brady et al. | |
| 8,852,205 B2 | 10/2014 | Brady et al. | |
| 9,301,769 B2 | 4/2016 | Brady et al. | |
| 9,351,749 B2 | 5/2016 | Brady et al. | |
| 9,402,707 B2 | 8/2016 | Brady et al. | |
| 9,433,429 B2 | 9/2016 | Vale et al. | |
| 9,445,829 B2 | 9/2016 | Vale et al. | |
| 9,463,036 B2 | 10/2016 | Brady et al. | |
| 9,642,635 B2 | 5/2017 | Vale et al. | |
| 9,642,639 B2 | 5/2017 | Brady et al. | |
| 10,034,680 B2 | 7/2018 | Brady et al. | |
| 10,080,575 B2 | 9/2018 | Brady et al. | |
| 10,201,360 B2 | 2/2019 | Vale et al. | |
| 10,265,086 B2 | 4/2019 | Vale et al. | |
| 10,278,717 B2 | 5/2019 | Brady et al. | |
| 10,285,720 B2 | 5/2019 | Gilvarry et al. | |
| 10,292,722 B2 | 5/2019 | Brady et al. | |
| 10,292,723 B2 | 5/2019 | Brady et al. | |
| 10,299,811 B2 | 5/2019 | Brady et al. | |
| 10,357,265 B2 | 7/2019 | Brady et al. | |
| 10,363,054 B2 | 7/2019 | Vale et al. | |
| 10,390,850 B2 | 8/2019 | Vale et al. | |
| 10,420,570 B2 | 9/2019 | Vale et al. | |
| 10,441,301 B2 | 10/2019 | Vale et al. | |
| 10,517,622 B2 | 12/2019 | Vale et al. | |
| 10,588,648 B2 | 3/2020 | Brady et al. | |

(Continued)

FOREIGN PATENT DOCUMENTS

WO 2011095352 A1 8/2011

*Primary Examiner* — Kankindi Rwego
(74) *Attorney, Agent, or Firm* — WOMBLE BOND DICKINSON (US) LLP

(57) ABSTRACT

A mechanical thrombectomy device includes several clot arrestors mounted on a support wire. The clot arrestors have rings of expandable frame cells. The frame cell rings include an open frame cell ring, having a gap between adjacent frame cells in the ring, and a closed frame cell ring, having no gap between adjacent frame cells. The gap allows clots to enter the clot arrestor for retrieval from a target anatomy. Other embodiments are also described and claimed.

19 Claims, 12 Drawing Sheets

(56) References Cited

U.S. PATENT DOCUMENTS

| | | | |
|---|---|---|---|
| 10,588,649 B2 | 3/2020 | Brady et al. | |
| 10,610,246 B2 | 4/2020 | Brady et al. | |
| 10,617,435 B2 | 4/2020 | Vale et al. | |
| 10,667,833 B2 | 6/2020 | Vale et al. | |
| 10,675,045 B2 | 6/2020 | Brady et al. | |
| 10,682,152 B2 | 6/2020 | Vale et al. | |
| 10,582,939 B2 | 7/2020 | Brady et al. | |
| 10,743,894 B2 | 8/2020 | Brady et al. | |
| 10,792,055 B2 | 10/2020 | Brady et al. | |
| 10,792,056 B2 | 10/2020 | Vale et al. | |
| 10,842,498 B2 | 11/2020 | Vale et al. | |
| 11,197,684 B1* | 12/2021 | Ngo | A61B 17/221 |
| 2002/0161393 A1 | 10/2002 | Demond et al. | |
| 2007/0288054 A1* | 12/2007 | Tanaka | A61B 17/221 |
| | | | 606/200 |
| 2008/0167678 A1 | 7/2008 | Morsi | |
| 2008/0275490 A1 | 11/2008 | Fleming | |
| 2010/0161033 A1* | 6/2010 | Jantzen | A61L 31/148 |
| | | | 623/1.2 |
| 2010/0268264 A1* | 10/2010 | Bonnette | A61F 2/0108 |
| | | | 606/200 |
| 2012/0209311 A1* | 8/2012 | Grandfield | A61B 17/221 |
| | | | 606/200 |
| 2013/0144326 A1 | 6/2013 | Brady et al. | |
| 2013/0184739 A1 | 7/2013 | Brady et al. | |
| 2013/0345739 A1 | 12/2013 | Brady et al. | |
| 2014/0379023 A1 | 12/2014 | Brady et al. | |
| 2015/0032121 A1 | 1/2015 | Janardhan et al. | |
| 2016/0058458 A1 | 3/2016 | Hansen et al. | |
| 2016/0066921 A1 | 3/2016 | Seifert et al. | |
| 2018/0263632 A1 | 9/2018 | Seifert et al. | |
| 2018/0344338 A1 | 12/2018 | Brady et al. | |
| 2019/0000492 A1 | 1/2019 | Casey et al. | |
| 2019/0142442 A1 | 5/2019 | Vale et al. | |
| 2019/0167287 A1 | 6/2019 | Vale et al. | |
| 2019/0201014 A1 | 7/2019 | Vale et al. | |
| 2019/0223893 A1 | 7/2019 | Gilvarry et al. | |
| 2019/0231372 A1 | 8/2019 | Brady et al. | |
| 2019/0239907 A1 | 8/2019 | Brady et al. | |
| 2019/0239908 A1 | 8/2019 | Brady et al. | |
| 2019/0239910 A1 | 8/2019 | Brady et al. | |
| 2019/0298397 A1 | 10/2019 | Vale et al. | |
| 2019/0328411 A1 | 10/2019 | Vale et al. | |
| 2019/0336151 A1 | 11/2019 | Vale et al. | |
| 2019/0365399 A1 | 12/2019 | Vale et al. | |
| 2020/0000483 A1 | 1/2020 | Brady et al. | |
| 2020/0046390 A1 | 2/2020 | Brady et al. | |
| 2020/0060703 A1 | 2/2020 | Vale et al. | |
| 2020/0100804 A1 | 4/2020 | Casey et al. | |
| 2020/0107851 A1 | 4/2020 | McCarthy | |
| 2020/0121339 A1 | 4/2020 | Brady et al. | |
| 2020/0246031 A1 | 8/2020 | Vale et al. | |
| 2020/0281611 A1 | 9/2020 | Kelly et al. | |
| 2020/0281612 A1 | 9/2020 | Kelly et al. | |
| 2020/0305900 A1 | 10/2020 | Vale et al. | |
| 2020/0323615 A1 | 10/2020 | Casey et al. | |
| 2020/0345904 A1 | 11/2020 | Casey et al. | |
| 2020/0353205 A1 | 11/2020 | Kelly et al. | |
| 2020/0353226 A1 | 11/2020 | Keating et al. | |
| 2020/0353228 A1 | 11/2020 | Casey et al. | |
| 2020/0353229 A1 | 11/2020 | Casey et al. | |
| 2021/0378693 A1* | 12/2021 | Atchaneeyasakul | A61B 90/39 |
| 2023/0131129 A1* | 4/2023 | Wack | A61F 2/852 |
| | | | 623/1.13 |

* cited by examiner

THROMBECTOMY DEVICE HAVING OPEN FRAME CELL RING

BACKGROUND

Field

The present disclosure relates to thrombectomy devices used for ischemic stroke treatments. More specifically, the present disclosure relates to mechanical thrombectomy devices used for neurovascular thrombectomy procedures.

Background Information

Several classes of devices exist for salvaging the brain of patients suffering from acute ischemic stroke. Among the classes are mechanical thrombectomy devices, which are used to remove thrombi from the neurovasculature to restore perfusion through an initially occluded artery. Mechanical thrombectomy devices that have been cleared for such use include coil retrievers, aspiration devices, and more recently, stent retriever devices.

Existing stent retriever devices are essentially self-expanding stents that can be deployed within a thrombus to push the thrombus aside and/or entangle the thrombus within struts of the stent. After mechanically integrating with the thrombus, the stent and thrombus can be withdrawn into a delivery catheter and removed from the patient. Important factors in the usability and performance of stent retriever devices include their ability to capture or engage a clot, their ability to retain the captured or engaged clot as the device is retracted through tortuous vasculature, and their ability to balance radial strength with vessel apposition. Shortcomings in these factors can extend procedural times and reduce clinical success rates.

SUMMARY

Existing stent retriever devices provide suboptimal clot engagement, clot retention, and/or vessel interaction. More particularly, stent retriever devices today utilize a unitary stent body that hinders clot capture and engagement. For example, the unitary stent body can roll over and pass by a hard clot, thereby bouncing off of the clot rather than engaging or capturing the clot. Furthermore, the unitary stent body may attempt to achieve sufficient radial strength to engage the clot by fully apposing the vessel using a metal-to-artery ratio that is aggressive to the target anatomy.

A mechanical thrombectomy device is described below, which addresses the shortcomings of existing stent retriever devices described above. In an embodiment, the mechanical thrombectomy device includes a support wire, a first clot arrestor, and a second clot arrestor. The first clot arrestor is mounted on the support wire and has a first closed frame cell ring and a first open frame cell ring. The second clot arrestor is mounted on the support wire and has a second closed frame cell ring and a second open frame cell ring. The open frame cell rings allow a clot to migrate into an interior of the clot arrestor for clot engagement and retention.

In an embodiment, the mechanical thrombectomy device includes a support wire, a first clot arrestor, and a second clot arrestor. The first clot arrestor is mounted on the support wire and has a first frame cell ring including a first frame cell having a different radial strength than a second frame cell. The second clot arrestor is mounted on the support wire distal to or proximal to the first clot arrestor. The varying radial strengths of the frame cells provide a corrugated profile that engages clots without fully apposing or injuring a vessel.

In an embodiment, the mechanical thrombectomy device includes a support wire, a first clot arrestor, and a second clot arrestor. The first clot arrestor is mounted on the support wire. The first clot arrestor includes an outer frame cell ring concentric and longitudinally aligned with an inner frame cell ring. The outer frame cell ring has an inner surface apposed to an outer surface of the inner frame cell ring. The second clot arrestor is mounted on the support wire distal to or proximal to the first clot arrestor. The nested frame cell rings generate sufficient radial strength to engage clots with less vessel contact, thereby reducing a risk of injuring a vessel.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
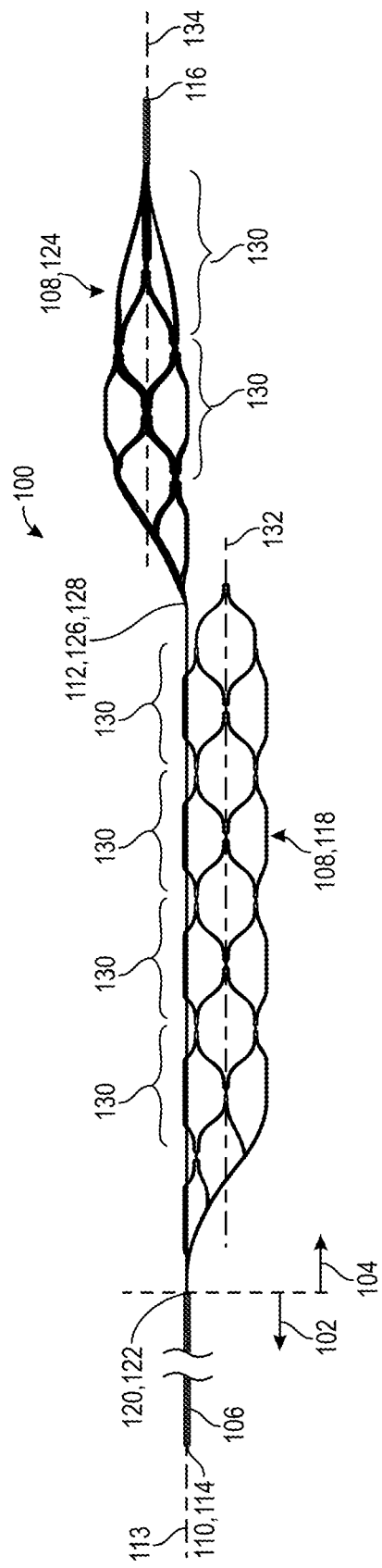
FIG. 1 is a plan view of a mechanical thrombectomy device deployed in free space, in accordance with an embodiment.

Embodiments describe a mechanical thrombectomy device having clot arrestors independently mounted on a support wire. The mechanical thrombectomy device can be used to treat acute ischemic stroke. The mechanical thrombectomy device may, however be used in other applications, such as removal of clots from other vessels.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction along a longitudinal axis of a support wire or clot arrestor. Similarly, "proximal" may indicate a second direction opposite to the first direction. Such terms are provided to establish relative frames of reference, however, and are not intended to limit the use or orientation of a mechanical thrombectomy device to a specific configuration described in the various embodiments below.

In an aspect, a mechanical thrombectomy device includes several clot arrestors mounted on a support wire. The clot arrestors are independently mounted. Each of the clot arrestors includes at least one frame cell ring that is open, e.g., has a slot between adjacent frame cells in the ring. The slot or opening provides a passage for a clot to pass from a vessel wall into an interior of the clot arrestor. Accordingly, the clot arrestors can capture and retrieve the clot.

In an aspect, at least one of the clot arrestors of the mechanical thrombectomy device includes a frame cell that has a different radial strength than another frame cell in a same frame cell ring. For example, a first frame cell circumferentially adjacent to a second frame cell can have a higher radial strength than the second frame cell. The differing radial strengths of the frame cells can cause one frame cell to bias outward into contact with a vessel wall and another frame cell to bias inward away from the vessel wall. For example, the first frame cell can press outward against the vessel wall and the second frame cell can bow inward away from the vessel wall. The resulting corrugated profile of the frame cell ring can provide sufficient radial strength to engage a clot while minimizing vessel wall contact to be less aggressive to the vessel.

In an aspect, the mechanical thrombectomy device includes a nested clot arrestor. More particularly, the clot arrestor can include an outer frame cell ring nested, or concentric and longitudinally aligned with, an inner frame cell ring. The nested frame cell rings can delivery combined radial force to a vessel wall. Only one of the rings, e.g., the outer frame cell ring, may be in contact with the vessel wall, however. The inner frame cell ring may be separated from the vessel wall by the outer frame cell ring. Accordingly, the clot arrestor can deliver sufficient radial force to engage a clot while reducing metal-to-artery ratio such that vessel wall contact is minimized to be less aggressive to the vessel.

Referring to FIG. 1, a plan view of a mechanical thrombectomy device deployed in free space is shown in accordance with an embodiment. A mechanical thrombectomy device 100 is an endovascular tool that can be used to treat acute ischemic stroke. The mechanical thrombectomy device 100 includes a proximal control region 102 used by an operator to advance, retract, and rotate a distal working region 104 of the device. More particularly, the mechanical thrombectomy device 100 includes a support wire 106 that the operator can push to advance the distal working region 104, pull to retract the distal working region 104, or twist to rotate the distal working region 104. The mechanical thrombectomy device 100 can include several clot arrestors 108 that can be advanced through and deployed from a microcatheter into a target anatomy. The clot arrestors 108, when deployed within the target anatomy, can capture, catch, engage, or mechanically integrate with a clot. The arrested clot can be retrieved from a patient by pulling the support wire 106 to retract the clot arrestors 108 and the clot from the vasculature.

In an embodiment, the support wire 106 includes a proximal wire end 110 and a distal wire end 112. The support wire 106 can extend longitudinally from the proximal wire end 110 to the distal wire end 112 along a wire axis 113. The support wire 106 can be a flexible elongated wire formed from a resilient material, such as stainless steel or a superelastic nickel titanium alloy, and thus, the wire axis may have one or more straight or curvilinear segments between the proximal wire end 110 and the distal wire end 112. A length of the support wire 106 may be less than an overall length of the mechanical thrombectomy device 100. For example, the distal wire end 112 may be located distal to at least one of the clot arrestors 108, and proximal to a distal end of at least one of the clot arrestors 108. Accordingly, a distance from the proximal wire end 110 (at a proximal device end 114) to the distal wire end 112 may be less than a distance from the proximal wire end 110 to a distal device end 116.

The clot arrestors are independently mounted on the support wire 106. More particularly, each clot arrestor 108 includes a respective expandable frame, and the respective expandable frames of the clot arrestors 108 are connected to the support wire 106 at respective locations. For example, a first clot arrestor 118 has a first expandable frame mounted on and connected to the support wire 106 at a first joint 120. The first joint 120 can be at a first location 122 along the support wire 106. A second clot arrestor 124 has a second expandable frame mounted on and connected to the support wire 106 at a second joint 126. The second joint 126 can be at a second location 128 along the support wire 106. The mechanical thrombectomy device 100 may have more than two clot arrestors 108. For example, the mechanical thrombectomy device 100 can have a third clot arrestor, a fourth clot arrestor, etc. The expandable frames of the clot arrestors 108 can be arranged in series in a longitudinal direction, e.g., along the wire axis 113, and each expandable frame can be independently supported on the support wire 106 relative to the other expandable frames.

The sequentially arranged clot arrestors 108 may have identical or different structures. For example, in the embodiment shown in FIG. 1, the most proximal clot arrestor, i.e., the first clot arrestor 118, and the distal clot arrestor, i.e., the second clot arrestor 124, can have geometries that differ. Some of these geometrical differences are described below, but it will be appreciated that one difference can be the presence of frame cell rings 130 having one or more openings or slots positioned differently along a length of the clot arrestors. Accordingly, the independently supported clot arrestors 108 can provide respective degrees of clot engagement, clot capture, flexibility, or any other performance attribute.

Each clot arrestor 108 can have a respective arrestor axis that is radially offset from the wire axis 113. For example, the centers of the clot arrestors 108 can define the respective arrestor axis, which may be a longitudinal axis extending longitudinally through the clot arrestor 108. More particularly, the first clot arrestor 118 can have a first longitudinal axis 132, providing a first arrestor axis, and the second clot arrestor 124 can have a second longitudinal axis 134, providing a second arrestor axis. Given that the arrestor axes, 132, 134, are radially spaced from the wire axis 113 (in a free state outside of a vessel), the clot arrestors 108 are eccentrically supported on the support wire 106. More particularly, the clot arrestors 108 can attach to the support wire 106 at the wire axis 113, but the expandable frames are eccentrically supported about the support wire 106.

In the free state, the support wire 106 can be linearly arranged, extending through one or more of the clot arrestors 108. For example, the support wire 106 can extend fully through the first, proximal, clot arrestor 118, and can terminate proximal to a distal end of the second, distal, clot arrestor 124. When the mechanical thrombectomy device 100 is in the free state, e.g., deployed in free space, the first longitudinal axis 132 of first clot arrestor 118 can be radially offset from the wire axis 113, as described above. Similarly, the second longitudinal axis 134 can be radially offset from the wire axis 113 in the freely deployed state. Furthermore, the clot arrestors 118, 124 can be eccentrically disposed relative to each other. Accordingly, when the mechanical thrombectomy device 100 is deployed in free space, the first longitudinal axis 132 of the first clot arrestor 118 can be in a non-coaxial relationship with the second longitudinal axis 134 of the second clot arrestor 124.

Figure 2:
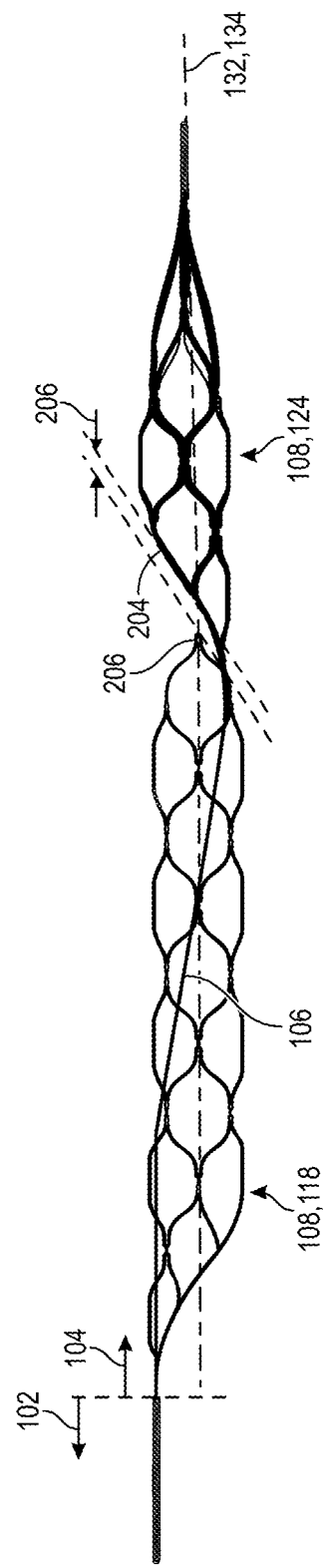
FIG. 2 is a plan view of a mechanical thrombectomy device deployed in a blood vessel, in accordance with an embodiment.

Referring to FIG. 2, a plan view of a mechanical thrombectomy device deployed in a blood vessel is shown in accordance with an embodiment. When the distal working region 104 is deployed in a blood vessel, a vessel wall applies a deforming load to move the clot arrestors 108 into a constrained state. In this case, the deforming load is a radial load, driving the arrestor axes into alignment in the radial direction. More particularly, when the mechanical thrombectomy device 100 is deployed in the blood vessel with the first clot arrestor 118 and the second clot arrestor 124 apposed to a vessel wall in the constrained state, the first longitudinal axis 132 can be forced into a coaxial relationship with the second longitudinal axis 134. Notably, the expandable frames are connected to the support wire 106 independently of each other. Accordingly, the clot arrestors 108 can deflect independently, e.g., the first clot arrestor 118 can move upward and the second clot arrestor 124 can move downward, to bring the longitudinal axes 132, 134 into alignment.

As the clot arrestors 108 align within the vessel, the support wire 106 is deflected into a non-linear shape. More particularly, a proximal segment of the support wire 106 in the proximal control region 102 may remain linear, e.g., straight, but given that the longitudinal axes 132, 134 are eccentrically located with respect to the wire axis 113, as the arrestor axes become more central, e.g., aligned with a central axis of the blood vessel, the distal segment of the support wire 106 in the distal working region 104 supporting the expandable frames may become non-linear, e.g., curved. More particularly, the wire axis 113 can become off-center, e.g., forced radially outward toward the vessel wall, and the distal segment of the support wire 106 may therefore take on a curvilinear shape that is different than the linear shape of the proximal segment of the support wire.

The clot arrestors 108, which align with each other concentrically along the vessel wall when the mechanical thrombectomy device 100 is deployed within the vessel, can conform closely to each other. More particularly, a distance between adjacent clot arrestors 108 may be minimized. The first clot arrestor 118, e.g., a proximal clot arrestor, can have a distal frame end 202 and the second clot arrestor 124, e.g., a distal clot arrestor distal to the first clot arrestor 118, can have a proximal frame end 204. The frame ends can be separated by a longitudinal gap 206. The distal frame end 202 can conform to the proximal frame end 204 such that the longitudinal gap 206 is minimized. More particularly, the longitudinal gap 206 between the distal frame end 202 and the proximal frame end 204 may be less than 10 mm at one or more locations around a circumference of the vessel wall. For example, the longitudinal gap 206 between the frame apices at the distal frame end 202 and a mouth of the second clot arrestor 124 at the proximal frame end 204 may be in a range of 1-10 mm, e.g., 1-5 mm.

A contour of the distal frame end 202 can have a same shape, extend parallel to, and/or conform to a contour of the proximal frame end 204. Here, the contour of the frame ends is defined by a profile or shape of an imaginary spline passing through the expandable frame of the respective clot arrestor 108 at the respective end. For example, the contour of the distal frame end 202 may be defined by an imaginary spline extending through a distalmost point of each of the distal cells (e.g., the cell apices) making up the first clot arrestor 118. Similarly, the contour of the proximal frame end 204 may be defined by an imaginary spline extending through the struts defining the mouth of the second clot arrestor 124. As shown, in profile, the contours can closely match or conform to each other. More particularly, the first clot arrestor 118 may be adjacent to the second clot arrestor 124 without the clot arrestors actually touching. The clot arrestors 108 can therefore match or conform to one another to approximate a continuous cylindrical body, even though there may be the longitudinal gap 206 separating the segments of the body.

Closely positioning the clot arrestors 108 and/or segments of the clot arrestors 108 can maximize the frame surface area that can engage clots along the vessel wall. It may be beneficial to provide a path for hard clots to move inward from the vessel wall into a lumen of the clot arrestors 108, however. In an embodiment, as described below, struts making up the frame cell rings at the distal frame end 202 and/or the proximal frame end 204 may be slotted, or open, to allow the ends to flex radially inward. More particularly, the slotted frame cell rings can be flexible enough to allow a hard clot to press against and deform the frame cell rings 130 radially inward. The distal end of the first clot arrestor 118 and/or the proximal end of the second clot arrestor 124 can flap inward to allow the hard clot to pass into the lumen of clot arrestors 108. Accordingly, by minimizing an axial distance between adjacent clot arrestors 108, in combination with the open frame cell rings describe below, an overall structure is provided that can effectively engage soft clots while allowing hard clots to be captured within the clot arrestors 108.

Figure 3:
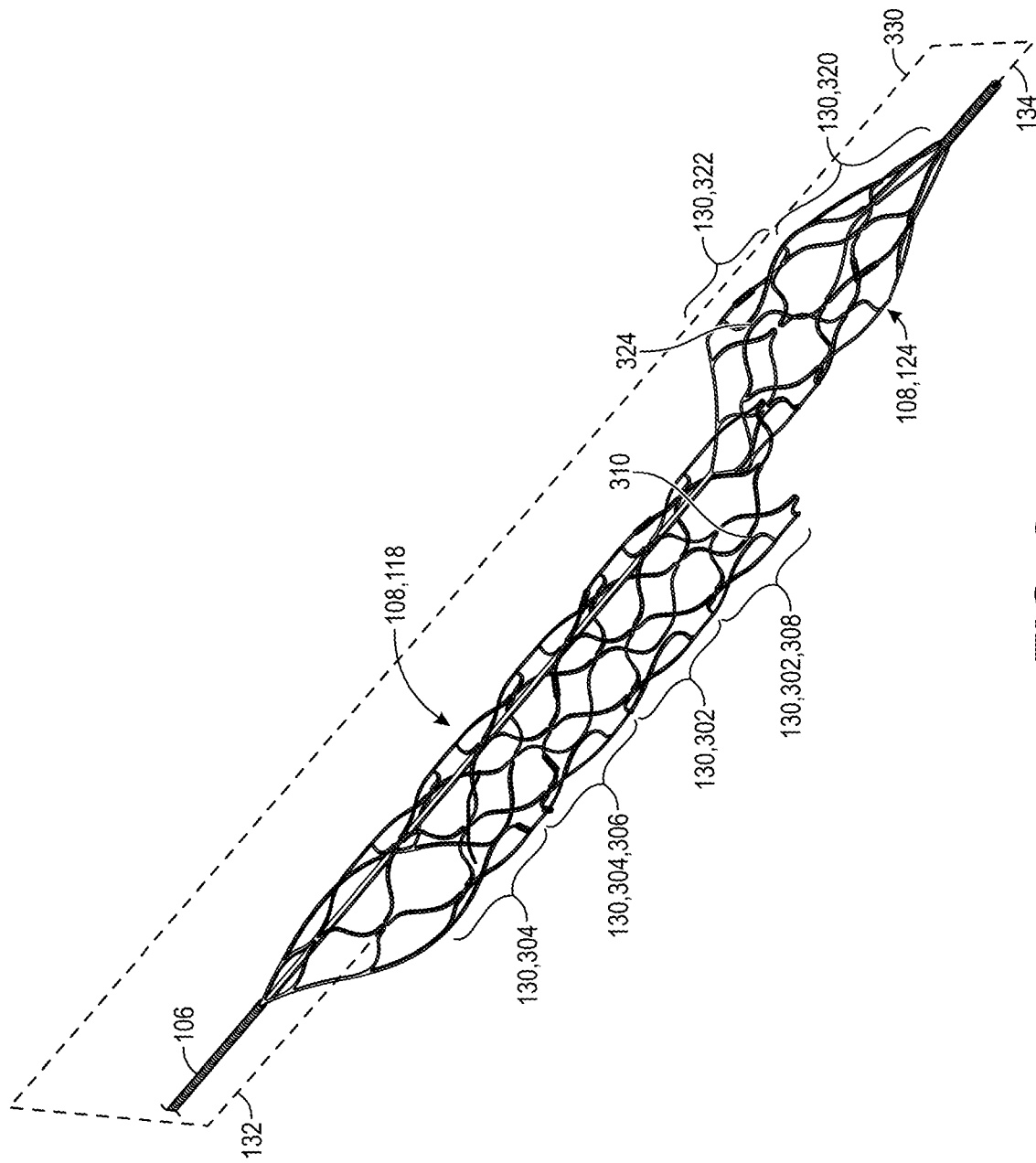
FIG. 3 is a perspective view of a distal portion of a mechanical thrombectomy device having several clot arrestors, in accordance with an embodiment.

Referring to FIG. 3, a perspective view of a distal portion of a mechanical thrombectomy device having several clot arrestors is shown in accordance with an embodiment. Each clot arrestor 108 can have a distal frame end and a proximal frame end. The frame ends can define openings into an interior channel of the respective clot arrestor 108. For example, the frame ends can provide a proximal opening into a cylindrical interior of the respective clot arrestor 108 and a distal opening into the cylindrical interior.

Each clot arrestor 108 can include at least one ring of frame cells. The frame cell rings 130 can be configured to expand and collapse. Geometrically, the expandable frames of the clot arrestors 108 can be similar to a stent. For example, the frame cell rings 130 can include two or more frame cells linked to each other in a circumferential direction to form a cylindrical expandable structure having an "open" or "closed" cell pattern. The cell pattern includes one or more slots, struts, or links to form an expandable structure having the proximal and/or distal opening into the cylindrical interior to capture and arrest a clot. As with stents, the clot arrestor 108 can be formed by laser-cutting the cell pattern from metal tubing. For example, the expandable frame can be a self-expanding structure formed from a shape memory alloy, e.g., nickel titanium tubing. Unlike stents, however, the radial force requirements of the expandable frame may be secondary to the structure shape, which can accommodate clot capture rather than act as a scaffold to prop open an atherosclerotic lesion.

Each clot arrestor 108 can include several frame cell rings 130, and each frame cell ring 130 may be characterized as an open frame cell ring 302 or a closed frame cell ring 304. Open frame cell rings 302 may be those rings that have circumferential discontinuities between two or more frame cells in the ring. Closed frame cell rings 304 may be those rings that have no circumferential discontinuities between frame cells in the ring. The structure of open and closed frame cell rings 304 is described further below. It will be understood that open frame cell rings 302 include slots or gaps that separate circumferentially adjacent frame cells. A clot can enter or migrate through the opening into the cylindrical interior of the clot arrestor 108.

In an embodiment, the first clot arrestor 118 has four or more frame cell rings 130. The frame cell rings 130 are interconnected in a longitudinal direction, e.g., stacked in the longitudinal direction, between a proximal end and a distal end of the first clot arrestor 118. The frame cell rings 130 of the first clot arrestor 118 can include at least one open frame cell ring 302 and at least one closed frame cell ring 304. More particularly, the first clot arrestor 118 can have a first closed frame cell ring 306 and a first open frame cell ring 308. The first open frame cell ring 308 can include a first gap 310 forming a circumferential discontinuity between circumferentially adjacent frame cells of the first open frame cell ring 308. The first closed frame cell ring 306 may lack a gap or circumferential discontinuity. For example, all frame cells in the closed frame cell ring may be connected to two adjacent frame cells.

The first closed frame cell ring 306 and the first open frame cell ring 308 can be two of the four or more frame cell rings 130 of the first clot arrestor 118. In an embodiment, at least half of the four or more rings of the first clot arrestor 118 are open frame cell rings 302. For example, the distal-most two frame cell rings in the first clot arrestor 118 can be open frame cell rings 302 having respective circumferential discontinuities, and the proximalmost two frame cell rings in the first clot arrestor 118 can be closed frame cell rings 304 having no circumferential discontinuities. The first clot arrestor 118 may therefore have a slot that extends through at least half a length of the clot arrestor 108. For example, an overall length of the clot arrestor 108 can be 40 mm, and the slot that divides frame cell rings over the clot arrestor length can extend over 25 mm or more.

The second clot arrestor 124, like the first clot arrestor 118, can include at least one open frame cell ring and at least one closed frame cell ring. In an embodiment, the second clot arrestor 124 includes a second closed frame cell ring 320 and a second open frame cell ring 322. The second closed frame cell ring 320 can have no circumferential discontinuities and the second open frame cell ring 322 can have one or more gaps, e.g., a second gap 324, forming a circumferential discontinuity in the frame cell ring 130. The second gap 324, like the first gap 310, can provide an entryway for clots to migrate into the cylindrical interior of the clot arrestor 108.

The first clot arrestor 118 and the second clot arrestor 124 can have axial and rotational relative positions. For example, the second clot arrestor 124 can be distal to (as shown in FIG. 3) or proximal to the first clot arrestor 118. In an embodiment, the first clot arrestor 118 is proximal to the second clot arrestor 124. As such, the first open frame cell ring 308, and the other frame cell ring(s) 130 of the first clot arrestor 118, can be proximal to the second open frame cell ring 322, and the other frame cell ring(s) 130 of the second clot arrestor 124.

The clot arrestors 108 may also have a relative rotational orientation. In an embodiment, a transverse plane 330 is defined by the support wire 106 (or the wire axis 113), the first longitudinal axis 132 of the first clot arrestor 118, and the second longitudinal axis 134 of the second clot arrestor 124 in the free state. Transverse plane 330 can be a vertical plane, for example. The transverse plane 330 may divide the clot arrestors 108 in half. More particularly, given that the transverse plane 330 passes through the respective clot arrestor axis, the plane can divide each clot arrestor 108 into a first half and a second half. In an embodiment, the transverse plane 330 passes through the one or more gaps of each clot arrestor 108. For example, the transverse plane 330 can extend through the first gap 310 in the first open frame cell ring 308 of the first clot arrestor 118. Similarly, the transverse plane 330 can extend through the second gap 324 in the second open frame cell ring 322 of the second clot arrestor 124. The gaps, i.e. the first gap 310 and the second gap 324, can be on opposite sides of the mechanical thrombectomy device 100. The first gap 310 can be at a lower side, e.g., at a six o'clock position along the transverse plane 330, and the second gap 324 can be at an upper side, e.g., at a twelve o'clock position along the transverse plane 330. Each gap may therefore be diametrically opposed to the wire axis 113 along the transverse plane 330.

Figure 4:
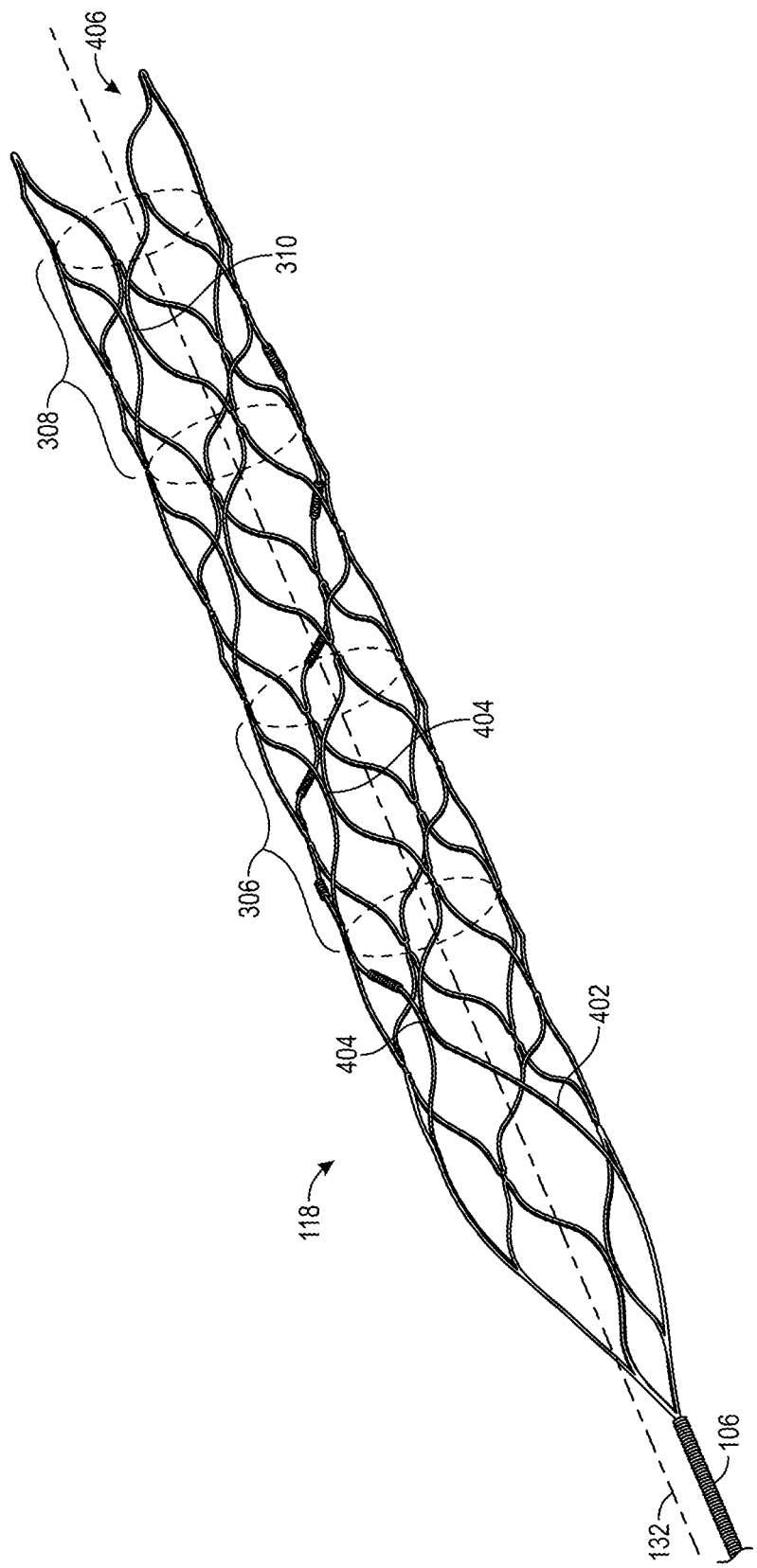
FIG. 4 is a perspective view of a first clot arrestor, in accordance with an embodiment.

Referring to FIG. 4, a perspective view of a first clot arrestor is shown in accordance with an embodiment. As described above, the first clot arrestor 118 can include the first closed frame cell ring 306 and the first open frame cell ring 308. The frame cell rings 130 can be longitudinally separated in the longitudinal direction along the first longitudinal axis 132. In an embodiment, the first open frame cell ring 308 is distal to the first closed frame cell ring 306. For example, the first open frame cell ring 308 can be farther from the joint between the first clot arrestor 118 and the support wire 106, as compared to a distance between the first closed frame cell ring 306 and the joint.

The first clot arrestor 118 can include a first arrestor mouth 402 at a proximal end of the arrestor. The first arrestor mouth 402 may be defined by several struts that curve outward from the joint at the support wire 106 to a ring connector 404. The frame cell ring 130 adjacent to, or defining, the first arrestor mouth 402 can be a closed frame cell ring 304. More particularly, every frame cell in the ring can be connected to circumferentially adjacent frame cells by ring connectors 404. The proximal end of the first clot arrestor 118 can therefore be a closed frame cell ring 304 such that the arrestor mouth is circumferentially continuous. The mouth may therefore hook a clot more easily. When the clot arrestor 108 is expanded, the arrestor mouth can capture thrombus and/or clots within the vessel.

The first clot arrestor 118 may also have a first distal opening 406. The first distal opening 406, like the first arrestor mouth 402, can be defined by struts extending around a circumference of the clot arrestor 108. The first distal opening 406 may, however, be circumferentially discontinuous. More particularly, the struts defining the first distal opening 406 can be portions of an open frame cell ring 302 that includes a gap 310 circumferentially between adjacent frame cells. The struts may therefore flex to allow clots to pass radially inward through the frame cell rings and into the first distal opening 406 to enter the cylindrical interior.

Figure 5:
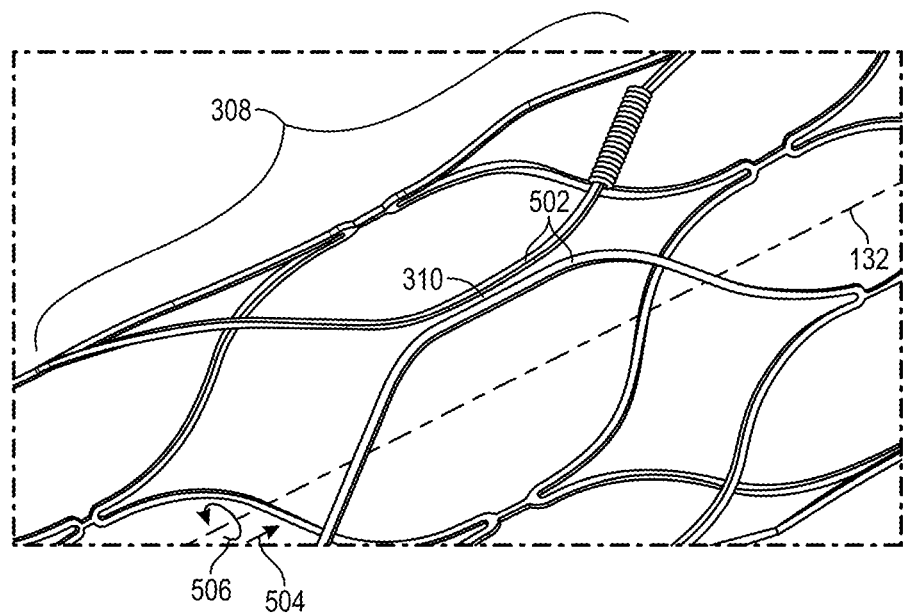
FIG. 5 is a perspective view of a first open frame cell ring of a first clot arrestor, in accordance with an embodiment.

Referring to FIG. 5, a perspective view of a first open frame cell ring of a first clot arrestor is shown in accordance with an embodiment. The first open cell frame ring can include the first gap 310 creating a discontinuity circumferentially within the ring of frame cells. A pair of struts 502 can extend adjacent to each other in a longitudinal direction 504, on either side of the first gap 310. The pair of struts 502 can be separated by the first gap 310 in a circumferential direction 506. The first gap 310 can therefore be a space extending radially outward from the cylindrical interior between the pair of struts 502 to a surrounding environment.

The break in the frame cell ring 308 can allow the frame cells to move relative to each other. More particularly, the pair of struts 502 can move farther or closer to each other to create a resilient and open frame cell ring 308. The resilient and open frame cell ring 308 can flex more easily under the pressure of a clot, for example. In such case, the clot can more easily move inward through the gap into the cylindrical interior. More particularly, the slot can allow the clot to push into the lumen of the mechanical thrombectomy device 100. The adjacent frame cells can flap down to allow the clot to press into and through the slit, even when the clot is too large to pass through any individual frame cell. Accordingly, the slit can provide for more forgiveness and flexibility that can help more effectively capture and retain clots than, for example, the closed frame cells.

The gaps in the open frame cells rings, e.g., the first gap 310, may be cuts or omissions in ring connectors 404. More particularly, the gaps can be small separations having respective gap widths. In an embodiment, the first gap 310 has a gap width that is less than three times a strut width of each of the pair of struts 502 that define the gap. For example, the gap may be on a same order of magnitude as the strut width.

Figure 6:
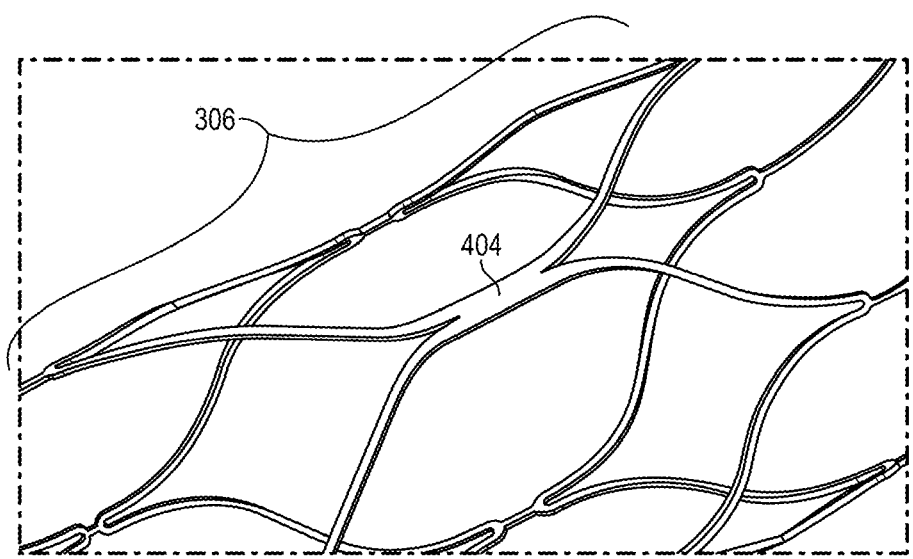
FIG. 6 is a perspective view of a first closed frame cell ring of a first clot arrestor, in accordance with an embodiment.

Referring to FIG. 6, a perspective view of a first closed frame cell ring of a first clot arrestor is shown in accordance with an embodiment. As opposed to the first open frame cell ring 308, the first closed frame cell ring 306 may have no gaps. More particularly, every frame cell in the frame cell ring 130 may be circumferentially interconnected with two adjacent frame cells (rather than one frame cell) by the ring connectors 404. The closed frame cell rings 304 may therefore have no discontinuities in the circumferential direction 506.

Figure 7:
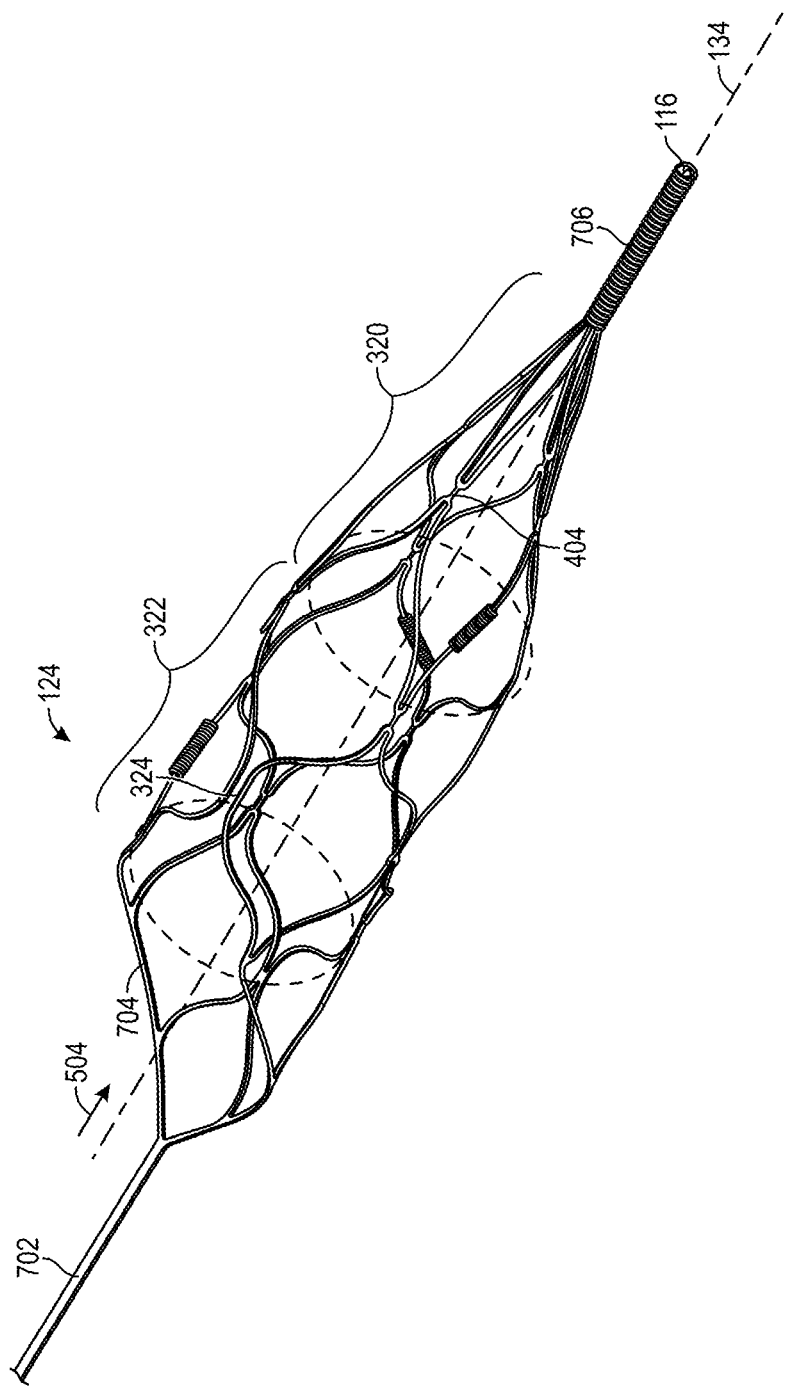
FIG. 7 is a perspective view of a second clot arrestor, in accordance with an embodiment.

Referring to FIG. 7, a perspective view of a second clot arrestor is shown in accordance with an embodiment. As described above, the second clot arrestor 124 can include the second closed frame cell ring 320 and the second open frame cell ring 322. The frame cell rings 130 can be longitudinally separated in the longitudinal direction 504 along the second longitudinal axis 134. In an embodiment, the second open frame cell ring 322 is proximal to the second closed frame cell ring 320. For example, the second open frame cell ring 322 can be farther from a stem 702 that connects the second clot arrestor 124 to the support wire 106, as compared to a distance between the second closed frame cell ring 320 and the stem 702. The stem 702 can include a linear member extending proximally from the proximal frame end 204 of the arrestor 124.

The second clot arrestor 124 can include a second arrestor mouth 704 at the proximal frame end 204. The second arrestor mouth 704 may be defined by several struts that curve outward from the stem 702 to proximal ends of the frame cells in the second open frame cell ring 322. More particularly, the frame cell ring 130 adjacent to, or defining, the second arrestor mouth 704 can be an open frame cell ring 302. The second arrestor mouth 704 may therefore be circumferentially discontinuous. The mouth may therefore expand to allow clots to push inward into the cylindrical interior of the clot arrestor 108. The clot arrestor 108 can capture thrombus and/or clots within the vessel.

The second clot arrestor 124 may have a distal coil tip 706. The distal coil tip 706 can extend to the distal device end 116. The distal coil tip 706 can be flexible and atraumatic to the vessel wall. The distal coil tip 706 can be radiopaque to provide improved visibility of the distal end of the second clot arrestor 124. For example, the distal coil tip 706 can be formed from stainless steel, platinum-iridium, or another radiopaque metal or material that is visible under fluoroscopy. In an embodiment, the distal coil tip 706 is joined to the expandable frame of the clot arrestor 108 by a mechanical, thermal, or adhesive joint. For example, the joint can be an adhesive joint, which bonds the distal coil tip 706 to the converging frame cells of the second clot arrestor 124.

Figure 8:
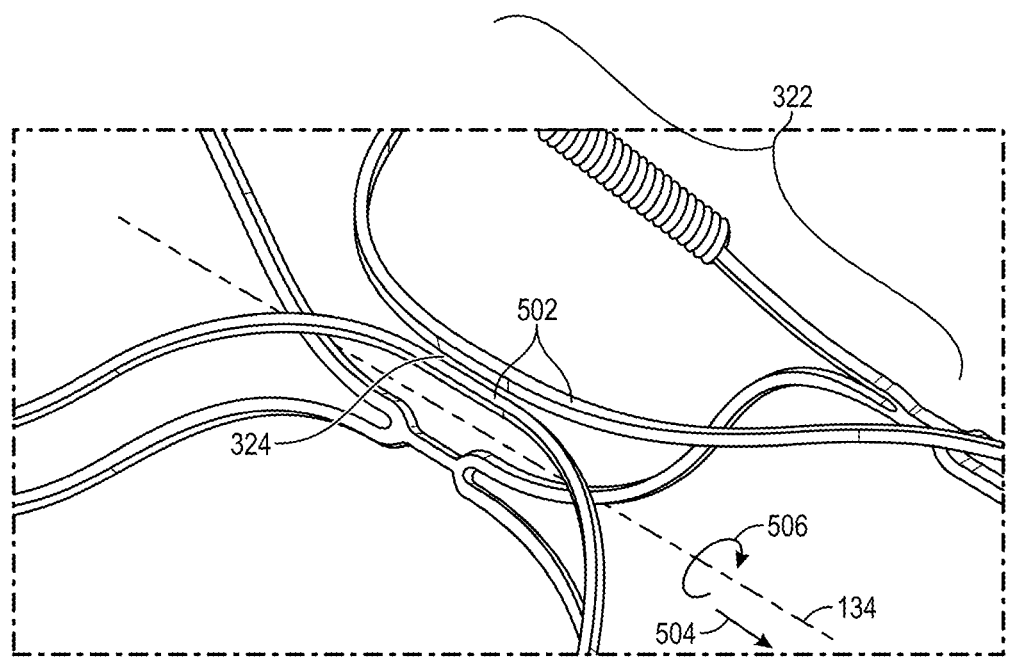
FIG. 8 is a perspective view of a second open frame cell ring of a second clot arrestor, in accordance with an embodiment.

Referring to FIG. 8, a perspective view of a second open frame cell ring of a second clot arrestor is shown in accordance with an embodiment. The second open cell frame ring can include the second gap 324 creating a discontinuity circumferentially within the ring of frame cells. More particularly, a pair of struts 502 can extend adjacent to each other in a longitudinal direction 504, on either side of the second gap 324. The pair of struts 502 can be separated by the second gap 324 in the circumferential direction 506. The second gap 324 can therefore be a space extending radially outward from the cylindrical interior between the pair of struts 502 to a surrounding environment. The break in the frame cell ring 130 can allow the frame cells to move relative to each other and to capture clots and/or thrombus in the manner described above with respect to the first open frame cell ring 308.

The gaps in the open frame cell rings, e.g., the second gap 324, may be cuts or omissions in ring connectors 404. More particularly, the gaps can be small separations having respective gap widths. In an embodiment, the second gap 324 has a gap width that is less than three times a strut width of each of the pair of struts 502 that define the second gap 324. For example, the second gap 324 may be on a same order of magnitude as the strut width.

Figure 9:
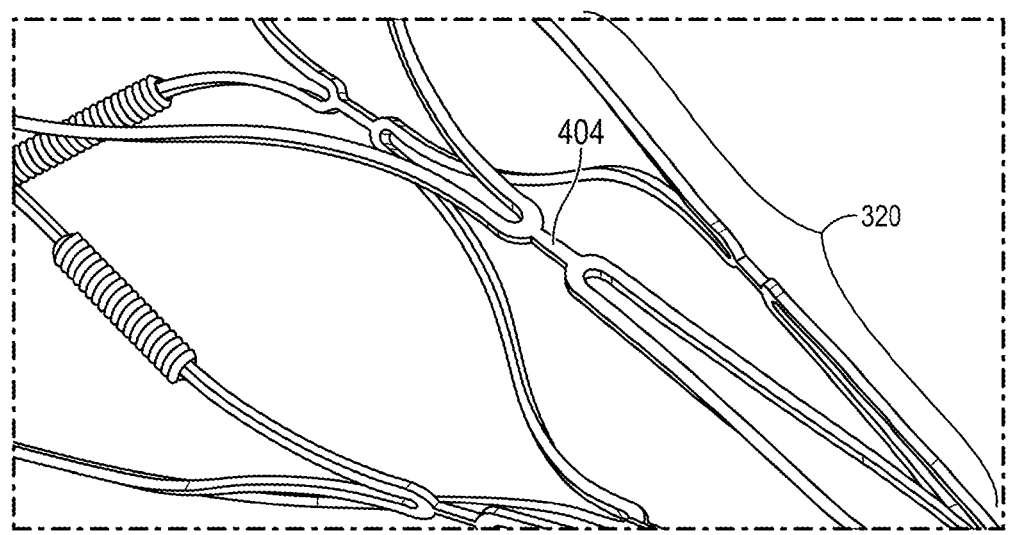
FIG. 9 is a perspective view of a second closed frame cell ring of a second clot arrestor, in accordance with an embodiment.

Referring to FIG. 9, a perspective view of a second closed frame cell ring of a second clot arrestor is shown in accordance with an embodiment. The second closed frame cell ring 320, like the first closed frame cell ring 306, can be circumferentially continuous. More particularly, every frame cell in the frame cell ring 130 may be interconnected with two adjacent frame cells (rather than one frame cell) by the ring connectors 404. The second closed frame cell ring 320 may therefore have no discontinuities in the circumferential direction 506.

Figure 15:
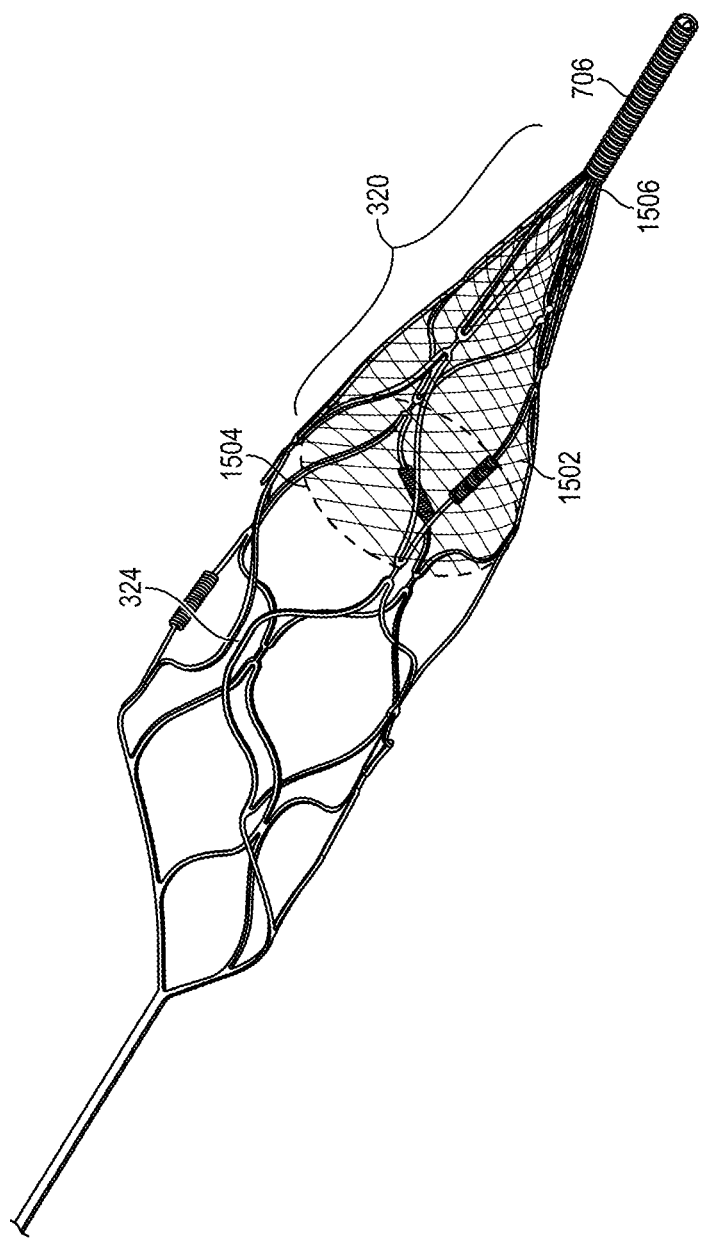
FIG. 15 is a perspective view of a filter mounted on a clot arrestor, in accordance with embodiment.

The second closed frame cell ring 320 can provide a relatively rigid structure, as opposed to the second open frame cell ring 322 having the discontinuity. The second closed frame cell ring 320 can therefore provide structural integrity to support a filter (FIG. 15). Furthermore, the relative rigidity can facility passing through the target anatomy by transmitting axial loads to the distal coil tip 706 that tracks through the vasculature.

Figure 10:
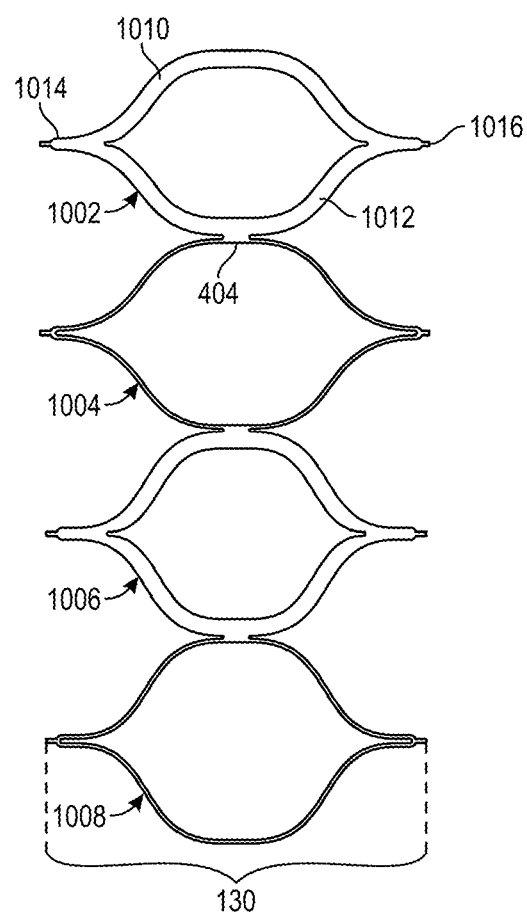
FIG. 10 is a plan view of a clot arrestor pattern including frame cells having variable radial strength, in accordance with an embodiment.

Referring to FIG. 10, a plan view of a clot arrestor pattern including frame cells having variable radial strength is shown in accordance with an embodiment. One or more clot arrestors 108 of the mechanical thrombectomy device 100 can have a corrugated design. More particularly, a cross-sectional profile of the clot arrestor 108, e.g., in an expanded state, can be corrugated in that some frame cells are radially outward to appose a vessel wall and some frame cells are radially inward away from the vessel wall. The corrugated profile has radial strength sufficient to engage a clot while also apposing the vessel wall over less than a full circumference of the vessel. The corrugated design can be achieved using a frame cell ring pattern that incorporates frame cells of differing radial strength, as described below.

In an embodiment, a frame cell ring 130 includes several frame cells, e.g., a first frame cell 1002, a second frame cell 1004, a third frame cell 1006, and a fourth frame cell 1008. The frame cells can have respective struts interconnected at respective apices. For example, the first frame cell 1002 can have a first strut 1010 and a second strut 1012, and the struts can meet at a proximal apex 1014 and a distal apex 1016. The frame cell ring 130 can interconnect with adjacent frame cell rings 130 at the apices, as shown. Furthermore, adjacent frame cells within the frame cell ring 130 can be interconnected. For example, the first frame cell 1002 can connect to the second frame cell 1004 at the ring connector 404. Such connection makes the adjacent frame cells circumferentially continuous with each other.

Each of the frame cells in the frame cell ring 130 can have respective radial strengths. For example, the first frame cell 1002 can have a higher radial strength than the second frame cell 1004. Radial strength of the respective frame cells may be achieved through cell pattern characteristics. For example, the first strut 1010 and the second strut 1012 of the first frame cell 1002 can be thicker or wider than the struts of the second frame cell 1004. Alternatively, curvature of the struts or other cell pattern features may be used to achieve respective cell radial strengths. In an embodiment, frame cells can have different cell area, e.g., one frame cell can have a larger area than an adjacent frame cell. In any case, the radial strength of the first frame cell 1002 can be different, e.g., higher or lower, than the radial strength of the second frame cell 1004. Similarly, the radial strengths of the third frame cell 1006 and the fourth frame cell 1008 can be different than each other and/or different than one or more of the first frame cell 1002 and the second frame cell 1004.

Figure 11:
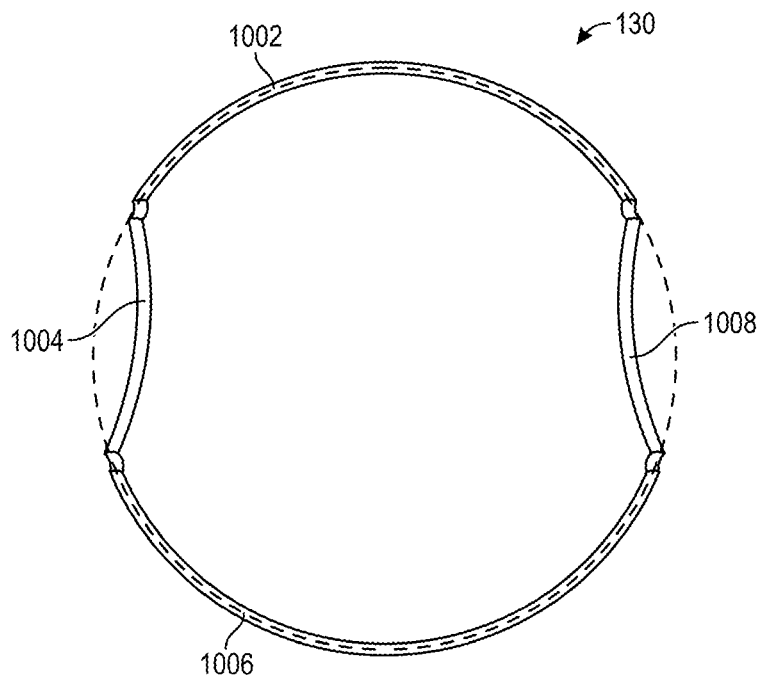
FIG. 11 is an end view of a clot arrestor having a corrugated profile deployed in a blood vessel, in accordance with an embodiment.

Referring to FIG. 11, an end view of a clot arrestor having a corrugated profile deployed in a blood vessel is shown in accordance with an embodiment. The varying radial strength of the frame cells can cause the clot arrestor 108 to have a corrugated shape upon expansion within the vessel. For example, the second frame cell 1004 may be biased or bowed radially inward relative to the first frame cell 1002. The outward bias of one or more frame cells combined with the inward bias of one or more frame cells results in a profile that undulates, or has peaks and grooves. Such a corrugated profile causes some frame cells to contact a vessel wall and others to not contact the vessel wall in the constrained state. More particularly, frame cells with higher radial strength can appose the vessel wall and frame cells with lower radial strength may not appose the vessel wall. The clot arrestor 108 may therefore apply sufficient radial strength to engage a clot without placing undue stress on the vessel wall.

In addition to balancing clot engagement against delicate treatment of the vessel, the corrugated design may also promote easier delivery of the clot arrestor 108 into the vessel. The mechanical thrombectomy device 100 can be delivered into the target anatomy through a microcatheter. More particularly, the clot arrestor 108 may be pushed through a lumen of the microcatheter. The lumen can be small, e.g., having a diameter of 0.017-0.021 inches. To fit within the small lumen, the clot arrestor 108 can be crimped or reduced in diameter and then slid through the lumen. In the contracted state, within the lumen, an outer surface of the clot arrestor 108 can contact a wall of the microcatheter. Such contact generates friction, which can resist forward movement of the clot arrestor 108. In an embodiment, the corrugated profile of the clot arrestor 108 can be present in the contracted state. Accordingly, less than a full circumference of the profile may be in contact with the wall during delivery. The reduced contact may translate into lower friction and, thus, improved deliverability of the clot arrestor 108 through the microcatheter to the target anatomy.

Figure 12:
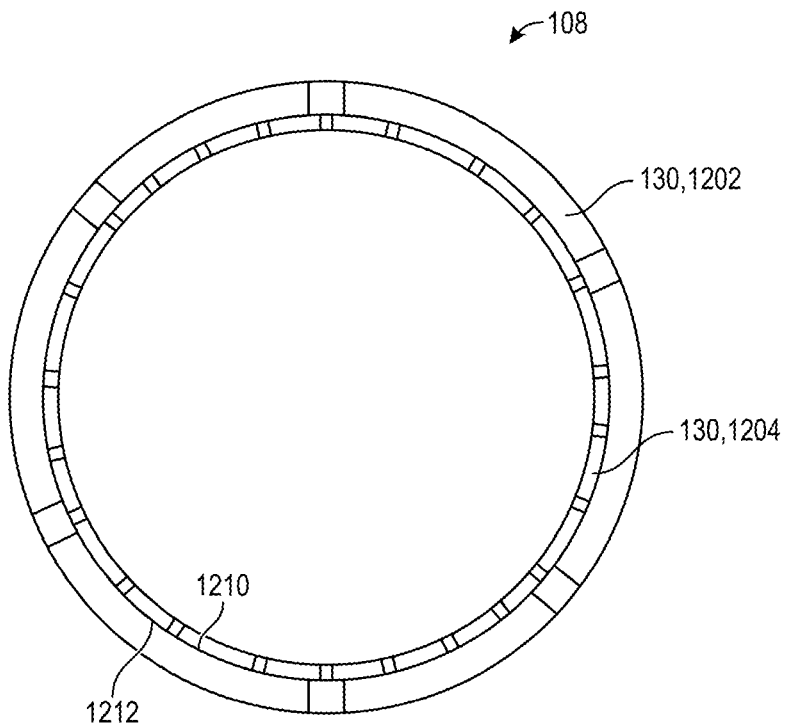
FIG. 12 is an end view of a clot arrestor having nested frame cell rings, in accordance with an embodiment.

Referring to FIG. 12, an end view of a clot arrestor having nested frame cell rings is shown in accordance with an embodiment. The corrugated design described above, which maintains effective radial force without fully apposing the vessel wall, provides reduced contact between the clot arrestor 108 and the vessel wall. Such contact can be quantified by a metal-to-artery ratio. The metal-to-artery ratio can be a ratio of an outward facing surface area of a clot arrestor that contacts a vessel wall during deployment compared to a total circumferential area of the vessel wall that surrounds the clot arrestor. Sufficient radial strength combined with reduced metal-to-artery ratio may also be achieved using a multi-layered stent.

In an embodiment, one or more of the clot arrestors 108 includes several frame cell rings 130 nested with each other. For example, the first clot arrestor 118 (or the second clot arrestor 124) can include an outer frame cell ring 1202 concentric and longitudinally aligned with an inner frame cell ring 1204. The outer frame cell ring 1202 can be a frame cell ring 130 having an outer surface radially outward from an outer surface 1212 of the inner frame cell ring 1204. For example, an inner surface 1210 of the outer frame cell ring 1202 can be apposed to and/or in contact with the outer surface 1212 of the inner frame cell ring 1204. The frame cell rings 130 may be nested. More particularly, the inner frame cell ring 1204 can be within the outer frame cell ring 1202. The frame cell rings 130 can be joined to each other. For example, one or more joints, e.g., adhesive or thermal welds, can connect the outer surface 1212 of the inner frame cell ring 1204 to the inner surface 1210 of the outer frame cell ring 1202 to fix the frame cell rings 130 relative to each other in the longitudinal direction 504.

The multi-layer design of the nested clot arrestor 108 frame cell rings 130 provides the outer frame cell ring 1202 that contacts the artery. The inner frame cell ring 1204, which is internal to the outer frame cell ring 1202, may not contact the artery. More particularly, the outer frame cell ring 1202 can extend circumferentially around the inner frame cell ring 1204 to separate the inner frame cell ring 1204 from the vessel wall. The inner frame cell ring 1204 can produce radial strength, e.g., outward pressure against the outer frame cell ring 1202, without contacting the vessel wall or increasing metal-to-artery ratio. More particularly, the outer frame cell ring 1202 that is radially outward of the inner frame cell ring 1204 can transmit radial force from the inner frame cell ring 1204, thereby providing approximately the same amount of radial strength as a single-layered clot arrestor 108 with less vessel contact.

Figure 13:
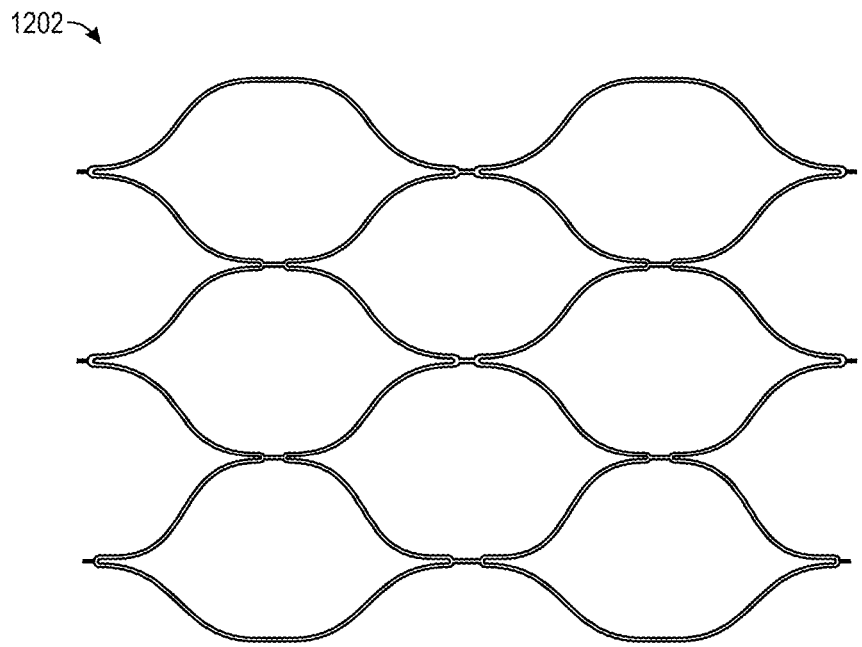
FIG. 13 is a plan view of a pattern of an outer frame cell ring having a relatively low metal-to-artery ratio, in accordance with an embodiment.

Referring to FIG. 13, a plan view of a pattern of an outer frame cell ring having a relatively low metal-to-artery ratio is shown in accordance with an embodiment. The outer frame cell ring 1202 can have a different metal-to-artery ratio than the inner frame cell ring 1204. Lower metal-to-artery ratio may be achieved by reducing the surface area of the outer surface of the outer frame cell ring 1202. For example, the outer frame cell ring 1202 can have a lower metal-to-artery ratio than the inner frame cell ring 1204. That is, the surface area of the outer surface 1212 of the inner frame cell ring 1204 may be lower than the surface area of the outer surface of the outer frame cell ring 1202. The surface area of the outer frame cell ring 1202 is represented by the strut pattern. The struts of the outer frame cell ring 1202 can have lower widths, for example, than struts of the inner frame cell ring 1204 shown in FIG. 14.

Figure 14:
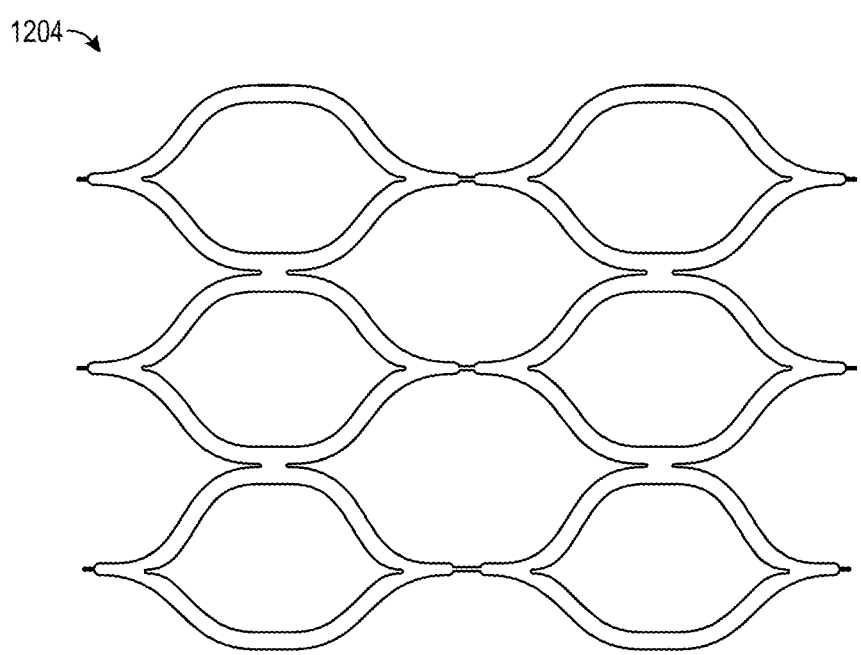
FIG. 14 is a plan view of a pattern of an inner frame cell ring having a relatively high metal-to-artery ratio, in accordance with an embodiment.

Referring to FIG. 14, a plan view of a pattern of an inner frame cell ring having a relatively higher metal-to-artery ratio is shown in accordance with an embodiment. The outer surface 1212 of the inner frame cell ring 1204 has a larger surface area, as compared to the thinner strut pattern of the outer frame cell ring 1202 shown in FIG. 13. The inner frame cell ring 1204 can be separated from the vessel wall by the outer frame cell ring 1202. Thus, the combined frame cell rings 130 can press outward with combined force, while only contacting the vessel with the surface of the outer frame cell ring 1202. Such combined action can balance radial strength, to effectively engage a clot, with vessel contact, to reduce a risk of vessel trauma. The nested design can also improve deliverability by reducing friction within a microcatheter, similar to the benefits provided by the corrugated design.

Referring to FIG. 15, a perspective view of a filter mounted on a clot arrestor is shown in accordance with embodiment. The mechanical thrombectomy device 100 can include a filter 1502 mounted on the second closed frame cell ring 320. The filter 1502 can capture clots that pass distal to the expandable frames of the clot arrestors 108. In an embodiment, the filter 1502 is coupled to the second closed frame cell ring 320. For example, the filter 1502 can be mounted on the struts that form the closed cell ring. The filter 1502 can have a distally converging geometry. More particularly, the filter 1502 can extend distally from a proximal filter end 1504 to a distal filter end 1506, and the proximal filter end can have a larger transverse dimension than the distal filter end 1506. The converging geometry can form a closed structure to traverse a lumen of the blood vessel and capture any clots or portions of clots that pass distal to the expandable frames.

The filter 1502 is represented in FIG. 15 with cross-hatching, which can represent various filter materials. In an embodiment, the filter 1502 includes a web or a mesh structure. For example, the filter 1502 can be formed from a polymer or metal filament that is woven into a web or braided into a mesh having a distally-converging structure, such as a conical shape. The web or mesh can have a porosity that allows blood to pass, but captures clots or portions of clots that flow distal to the expandable frames. In an embodiment, the web or mesh is formed from a shape-memory material, such as a nickel titanium alloy, however, the filter 1502 may alternatively be formed from another material or metal, such as stainless steel.

Figure 16:
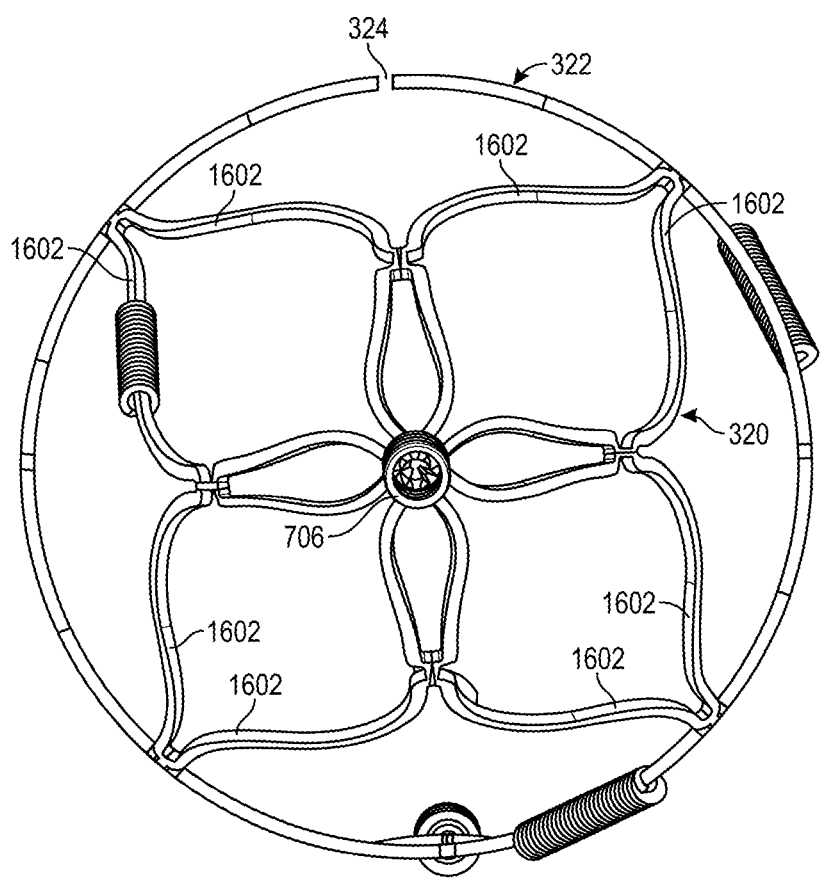
FIG. 16 is an end view of a clot arrestor having filter support struts, in accordance with embodiment.

Referring to FIG. 16, an end view of a clot arrestor is shown in accordance with embodiment. The end view omits the filter 1502 to more clearly illustrate the structure of the second closed frame cell ring 320 that underlies the filter 1502. In an embodiment, several filter support struts 1602 of the second closed frame cell ring 320 extend distally and radially inward toward the coil tip 706. More particularly, the filter support struts 1602 can extend from the second open frame cell ring 322 to a point of convergence at the arrestor axis. The filter support struts 1602 can maintain the filter 1502. More particularly, the filter 1502 can be connected to the struts, e.g., by joints, ties, etc. Accordingly, the filter 1502 can traverse the vessel lumen to capture any clots flowing distally therein.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A mechanical thrombectomy device, comprising:
    a support wire;
    a first clot arrestor mounted on the support wire and having a first closed frame cell ring and a first open frame cell ring, wherein the first open frame cell ring includes a first frame cell having a first longitudinal strut adjacent to a second frame cell having a second longitudinal strut, wherein the first longitudinal strut and the second longitudinal strut extend parallel to each other in a longitudinal direction separated by a circumferential gap to allow the first frame cell to move circumferentially relative to the second frame cell; and
    a second clot arrestor mounted on the support wire and having a second closed frame cell ring and a second open frame cell ring.

2. The mechanical thrombectomy device of claim 1, wherein the circumferential gap has a gap width less than three times a strut width of each of the first longitudinal strut and the second longitudinal strut.

3. The mechanical thrombectomy device of claim 1, wherein the first open frame cell ring is distal to the first closed frame cell ring.

4. The mechanical thrombectomy device of claim 3, wherein the second open frame cell ring is proximal to the second closed frame cell ring.

5. The mechanical thrombectomy device of claim 4, wherein the first clot arrestor is proximal to the second clot arrestor.

6. The mechanical thrombectomy device of claim 1, wherein a transverse plane is defined by the support wire, a first longitudinal axis of the first clot arrestor, and a second longitudinal axis of the second clot arrestor, and wherein the transverse plane extends through the circumferential gap between the first longitudinal strut and the second longitudinal strut of the first open frame cell ring and a second circumferential gap between second adjacent frame cells of the second open frame cell ring.

7. The mechanical thrombectomy device of claim 1, wherein the first clot arrestor has four or more frame cell rings including the first closed frame cell ring and the first open frame cell ring, and wherein at least half of the four or more frame cell rings are open frame cell rings.

8. The mechanical thrombectomy device of claim 1 further comprising a filter coupled to the second closed frame cell ring.

9. The mechanical thrombectomy device of claim 1, wherein the first clot arrestor and the second clot arrestor are independently mounted on the support wire such that a first longitudinal axis of the first clot arrestor is in a non-coaxial relationship with a second longitudinal axis of the second clot arrestor when the mechanical thrombectomy device is deployed in free space, and the first longitudinal axis is forced into a coaxial relationship with the second longitudinal axis when the mechanical thrombectomy device is deployed in a blood vessel with the first clot arrestor and the second clot arrestor apposed to a vessel wall.

10. A mechanical thrombectomy device, comprising:
a support wire;
a first clot arrestor mounted on the support wire and having a first frame cell ring including a plurality of first frame cells circumferentially continuous with and having a different cell pattern than a plurality of second frame cells such that the plurality of first frame cells have a higher radial strength than the plurality of second frame cells; and
a second clot arrestor mounted on the support wire distal to or proximal to the first clot arrestor.

11. The mechanical thrombectomy device of claim 10, wherein the plurality of second frame cells are biased radially inward relative to the plurality of first frame cells.

12. The mechanical thrombectomy device of claim 10, wherein the first clot arrestor is proximal to the second clot arrestor, wherein the first clot arrestor has a distal frame end and the second clot arrestor has a proximal frame end, and wherein the distal frame end conforms to the proximal frame end.

13. The mechanical thrombectomy device of claim 12, wherein a longitudinal gap between the distal frame end and the proximal frame end is less than 10 mm.

14. The mechanical thrombectomy device of claim 10, wherein the first clot arrestor and the second clot arrestor are independently mounted on the support wire such that a first longitudinal axis of the first clot arrestor is in a non-coaxial relationship with a second longitudinal axis of the second clot arrestor when the mechanical thrombectomy device is deployed in free space, and the first longitudinal axis is forced into a coaxial relationship with the second longitudinal axis when the mechanical thrombectomy device is deployed in a blood vessel with the first clot arrestor and the second clot arrestor apposed to a vessel wall.

15. A mechanical thrombectomy device, comprising:
a support wire;
a first clot arrestor mounted on the support wire, wherein the first clot arrestor includes an outer frame layer having a plurality of outer frame cell rings interconnected in a longitudinal direction and an inner frame layer having a plurality of inner frame cell rings interconnected in the longitudinal direction, wherein the outer frame layer is concentrically nested and longitudinally aligned with the inner frame layer, wherein the outer frame layer and the inner frame layer are formed from a non-resorbable metal, wherein the plurality of outer frame cell rings have a first outer surface and an inner surface apposed to a second outer surface of the plurality of inner frame cell rings, and wherein the second outer surface of the plurality of inner frame cell rings have a larger surface area than the first outer surface of the plurality of outer frame cell rings; and
a second clot arrestor mounted on the support wire distal to or proximal to the first clot arrestor.

16. The mechanical thrombectomy device of claim 15, wherein the plurality of outer frame cell rings extend circumferentially around the plurality of inner frame cell rings.

17. The mechanical thrombectomy device of claim 15, wherein the plurality of outer frame cell rings are radially outward of the plurality of inner frame cell rings.

18. The mechanical thrombectomy device of claim 17, wherein the plurality of outer frame cell rings have a lower metal-to-artery ratio than the plurality of inner frame cell rings.

19. The mechanical thrombectomy device of claim 15, wherein the first clot arrestor and the second clot arrestor are independently mounted on the support wire such that a first longitudinal axis of the first clot arrestor is in a non-coaxial relationship with a second longitudinal axis of the second clot arrestor when the mechanical thrombectomy device is deployed in free space, and the first longitudinal axis is forced into a coaxial relationship with the second longitudinal axis when the mechanical thrombectomy device is deployed in a blood vessel with the first clot arrestor and the second clot arrestor apposed to a vessel wall.

* * * * *